United States Patent [19]

Davis et al.

[11] 4,235,020
[45] Nov. 25, 1980

[54] INSPECTION SYSTEM FOR HEAT EXCHANGER TUBES

[75] Inventors: Clarence E. Davis; Daniel Hoyniak, both of Alliance, Ohio

[73] Assignee: The Babcock & Wilcox Company, New Orleans, La.

[21] Appl. No.: 35,190

[22] Filed: May 2, 1979

[51] Int. Cl.³ ............................ G01B 7/12; G01B 7/34
[52] U.S. Cl. ............................ 33/178 F; 33/DIG. 13
[58] Field of Search ......... 33/178 F, DIG. 13, 178 E; 324/233

[56] References Cited

U.S. PATENT DOCUMENTS

| | | | |
|---|---|---|---|
| 2,870,541 | 1/1959 | Mayes | 33/178 F |
| 2,933,819 | 4/1960 | Kinley | 33/178 F |
| 3,024,651 | 3/1962 | McGlasson | 33/178 F |

*Primary Examiner*—Willis Little
*Attorney, Agent, or Firm*—Robert J. Edwards; John F. Luhrs

[57] ABSTRACT

A system for inspecting the relatively long, thin-walled, small-bore tubes of a heat exchanger provided with support plates for holding the tubes in predetermined positions, comprising a composite scanner having a plurality of flexure springs contacting the interior surface of a tube for detecting and profiling tube abnormalities as the scanner traverses the tube and an eddy current sensor for generating a unique signal as the scanner passes a contiguous support plate to assist in the accurate location of tube abnormalities.

6 Claims, 7 Drawing Figures

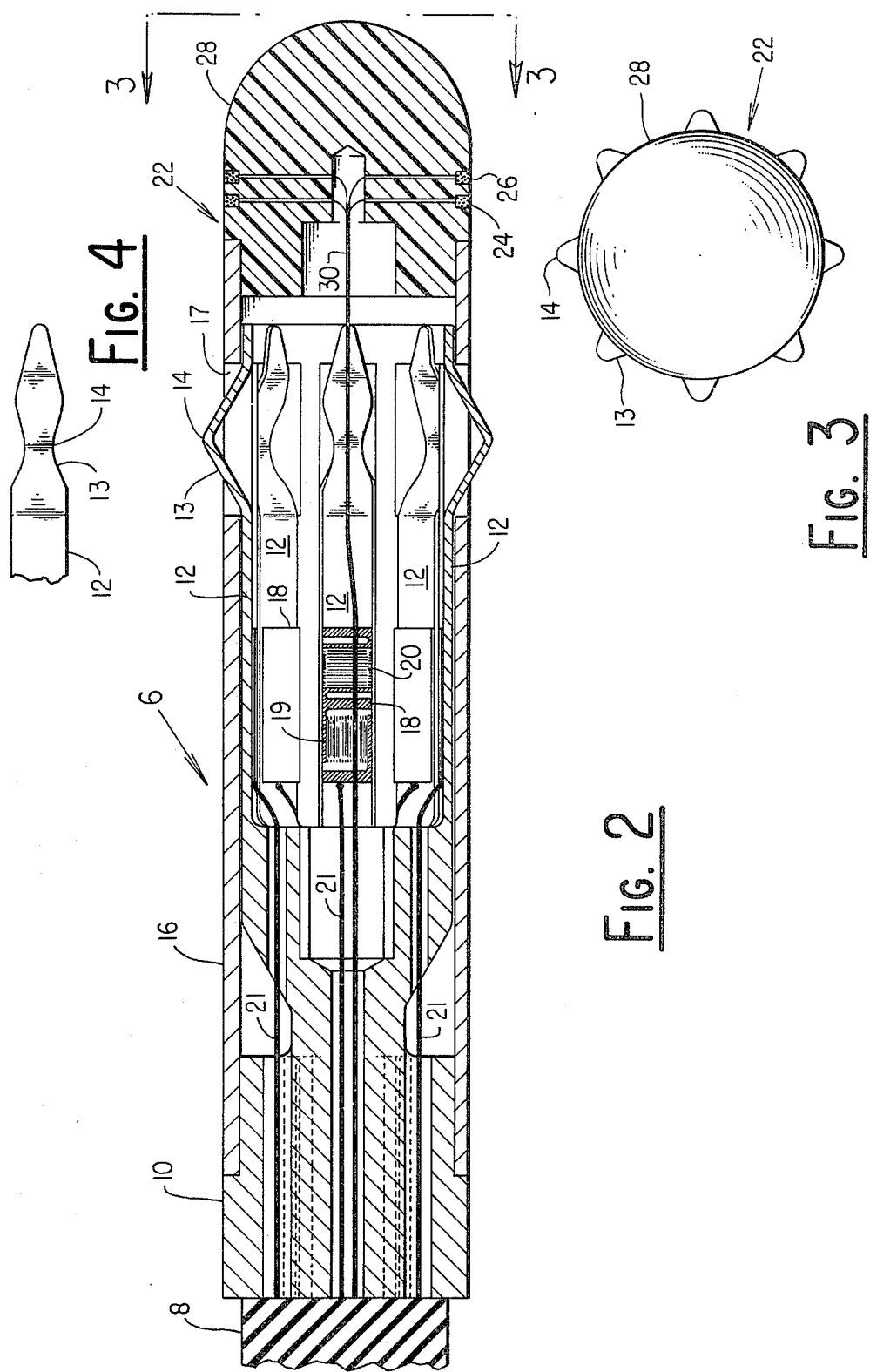

INSPECTION SYSTEM FOR HEAT EXCHANGER TUBES

This invention relates to an inspection system for determining, in-situ, the integrity of heat exchanger tubes. More particularly this invention relates to an inspection system for determining, in-situ, in heat exchanger tubes, the location, physical dimensions and character of abnormalities such as, but not limited to, dents, out-of-roundness, inside diameter variations and the like.

Of critical importance is the identification and measurement of such abnormalities in steam generators used in nuclear power producing units. Such generators may include upwards of sixteen thousand thin walled small bore tubes. As an order of magnitude, such tubes may have an O.D. of 0.625", a wall thickness of 0.034" and a length of 60' or more. The tubes are held in desired configuration within the generator by a plurality of support plates, distributed along their lengths and by relatively thick tube sheets at their ends, which also seal the interior from the exterior of the tubes.

Before being placed in service, and during operation it is essential that the tubes in such generators be free of significant abnormalities. It is therefore an established requirement that the tubes be inspected prior to being placed in service and periodically thereafter so that the location and physical dimensions of such abnormalities, if any, can be determined and a decision made as to the seriousness thereof and the corrective action to be taken.

The generation of eddy current signatures to locate and identify certain types of tube abnormalities is well established in the art. Reference may be made, for example, to U.S. Pat. No. 3,302,105 which illustrates and describes the eddy current signatures of various types of tube abnormalities which may be detected by this method. This method is not capable, however, of acurately measuring, as contrasted to detecting, the physical dimensions of tube abnormalities such as dents, and inside diameter variations.

It is therefore an object of this invention to provide an inspection system which will, in-situ, acurately locate and measure the size of tube abnormalities.

A further object of this invention is to provide a system for determining the inside diameter of a heat exchanger tube throughout its entire length.

Still another object of this invention is to provide a system for determining the out-of-roundness of a heat exchanger tube throughout its entire length.

A further object of this invention is to provide a tube inspection system which is simple to operate and requires a minimum of down time of the heat exchanger.

Another object of this invention is to provide a system whereby the inspection of heat exchanger tubes located in a hostile environment can be remotely controlled by an operator located in a benign environment.

These and other objects will be apparent from the following description when considered in connection with the drawings in which:

IN THE DRAWINGS

FIG. 2 is a longitudinal cross-section view of the composite scanner shown in FIG. 1.

FIG. 3 is an end view of the composite scanner taken along the line 3—3 of FIG. 2 in the direction of the arrows.

FIG. 4 is a fragmentary view of a spring finger.

DETAILED DESCRIPTION

Figure 1:
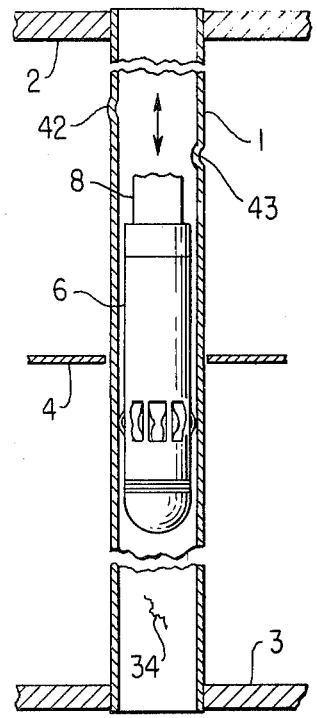
FIG. 1 is a schematic illustration of a composite scanner as applied to the in-situ inspection of a typical nuclear steam generator tube.

Referring to the drawings, wherein like reference characters designate like or corresponding parts throughout the several views, there is shown in FIG. 1 a cross section of a fragment of a tube 1, as incorporated in a nuclear steam generator, supported at its upper end by a tube sheet 2 and at its lower end by a tube sheet 3. The tube sheets 2 and 3 are welded to the tube 1 so that a fluid circulated through the tube, which may be the primary coolant, is isolated from the water and steam surrounding the exterior of the tube.

Distributed along the length of the tube are a plurality of support plates 4, holding the tube in desired position. The tube is not secured to the support plates by welding or the like, but passes through, with close tolerance, holes drilled or otherwise formed in the plates, which are also provided with passage ways for the flow of water and/or steam along the exterior of the tube. As a tube sheet may, for purposes of this invention, be considered a special type of support plate, the generic term "support plate" will hereinafter be used.

Shown within the tube 1 is a composite scanner 6 attached to a cable 8 for drawing the scanner through the tube at a selected speed, usually in the order of one foot per second. Various arrangements are known for drawing a scanner through a tube, one such arrangement, particularly adapted to the scanning of tubes in a nuclear steam generator, is illustrated and described in U.S. Pat. No. 4,172,492. In making a scan, the scanner is ordinarily positioned to one end of the tube, or to a predetermined bench mark, as, for example, a selected support plate, and then drawn through the tube by a remotely located drive mechanism (not shown) at the selected speed.

Referring to FIGS. 2 and 3 there is shown, respectively, the scanner 6 in longitudinal cross section and as viewed along the line 3—3 of FIG. 2 in the direction of the arrows. A cylindrical body 10 is provided with a plurality, in the embodiment shown, eight, cantilever, spring fingers 12, equally spaced about the circumference of the body. The spring fingers may be formed integral with the body or securely anchored thereto by any suitable means. Near the free end a section of each finger 12 is bent to form an outwardly extending crook 13, necked down to form a cusp 14, as shown in FIG. 4. In making a tube scan, the cusps 14 bear against the tube wall and follow changes in contour as may be caused by dents, diameter variations and the like. Preferably, but not essentially, the fingers 12 are enclosed in a protective sheath 16, secured to the body 10, and provided with openings 17 through which the crooks 13 project.

To each finger 12 there is secured, preferably at or near the point of maximum strain adjacent the body 10, a bi-axial strain gauge 18, provided with a winding 19 running parallel with the longitudinal center line of the finger and a winding 20 running at right angles to the center line. The resistance of winding 19 changes in proportion to changes in ambient temperature and the deflection of the spring finger from a null or neutral position. The resistance of winding 20 is substantially unaffected by deflection of the spring finger, but changes resistance in proportion to changes in ambient temperature. Each strain gauge winding is provided with leads, such as shown at 21, running through passageways formed in the base 10 and through the cable 8 to signal receiving instrumentation, to be described later.

Incorporated in the composite scanner 6 is an eddy current sensor, generally indicated at 22, comprised of differential windings 24, 26 housed in a body 28 of insulating material such as nylon, carried by and secured in the sheath 16. Leads 30 running through the body 10 and cable 8 transmit the signals generated by the eddy current sensor to the signal receiving instrumentation.

In traversing a tube, the cusps 14 as shown in FIG. 1 bear against the interior wall causing each spring finger 12 to bend from the predetermined null or normal position in accordance with variations in tube profile.

Figure 5:
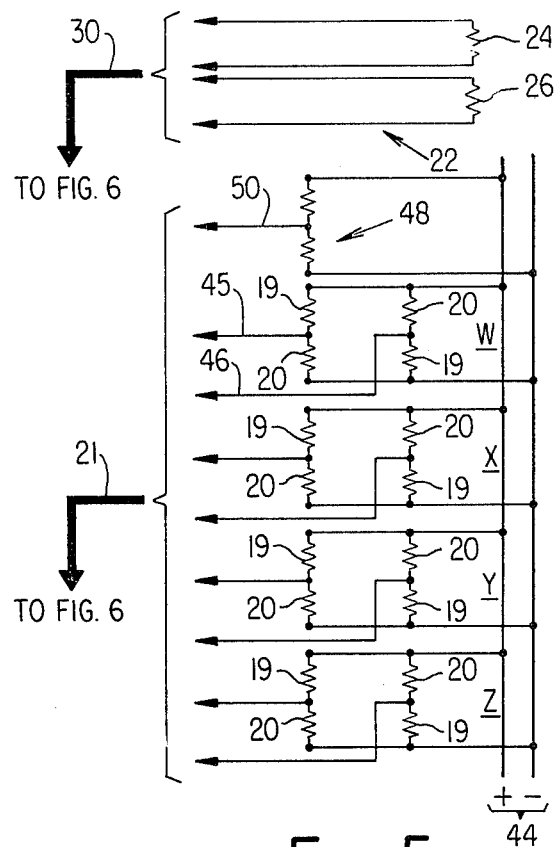
FIG. 5 is an elementary wiring diagram of the measuring circuits incorporated in the inspection system.

In FIG. 5, a circuit configuration is shown whereby, in traversing a tube, the deflection of each spring finger 12 from a null or normal position may be determined, or the algebraic sum of the deflections of any two spring fingers from a null or normal position may be determined. As ordinarily it is the algebraic sum of the deflection of diametrically opposite spring fingers which is of interest, there is shown in FIG. 5, the eight spring fingers incorporated in four bridge circuits identified as circuits W, X, Y, Z, and energized from a suitable source of potential 44, wherein the diametrically opposite strain gauges 19 are arranged in push-pull relationship. The potential difference, or bridge unbalance as it may be termed, appearing across leads 45–46 of any one of the bridge circuits is therefore a measure of the algebraic sum of the deflections of the diametrically opposite spring fingers 12. It is apparent that the algebraic sum of the deflections of any two spring fingers, as for example, adjacent spring fingers, can be determined by the potential difference between any two leads 45, two leads 46, or any combination of leads 45, 46.

Also incorporated in the circuit configuration is a voltage divider 48 generating a predetermined potential appearing in lead 50. Accordingly, changes in the difference in potentials between lead 50 and any one of the leads 45 or 46 of bridge circuits W, X, Y, Z will be a measure of the displacement of the spring finger from a null or normal position in traversing a tube. From the displacements of all of the spring fingers the shape of the tube at any one or all points in a traverse can be determined, and if any abnormalities so found are such as to jeopardize the integrity of the tube.

Figure 6:
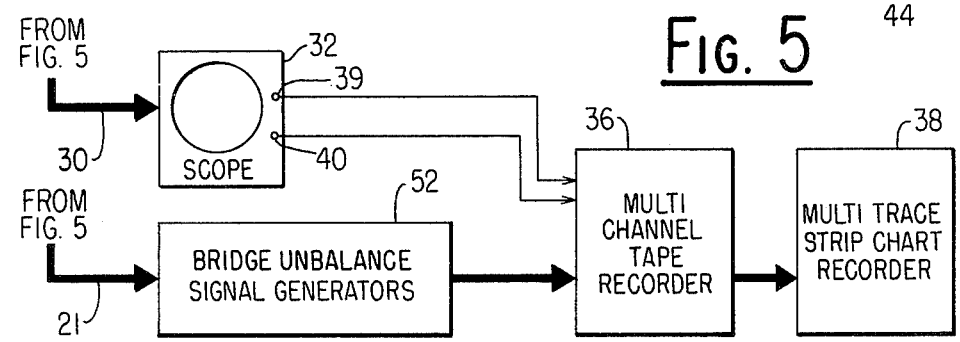
FIG. 6 is a block diagram of the read-out equipment incorporated in the inspection system.

The potential in lead 50 and the potentials in leads 45, 46 for each of the bridge circuits W, X, Y, Z, collectively identified as leads 21 in FIG. 5, are transmitted to suitable read-out devices such as shown in FIG. 6. Signals corresponding to bridge unbalances are generated in device 52, the number of such signal generators depending upon the particular type of tube scan. Thus, four such signal generators would be required to simultaneously read out the algebraic sum of the deflections of diametrically opposite spring fingers, whereas eight such generators would be required to simultaneously read out the deflection of each spring finger from a null or normal position. The signals generated in 52 can be transmitted to a variety of read-out devices as dictated by the exigencies of a particular application. As examples of such devices there is shown in FIG. 6 a tape recorder 36 and a strip chart recorder 38 responsive to the signals generated in the device 52. From the read-out devices such significant data as the inside tube radial dimensions at eight points at any one or all points in the tube traverse can be plotted or digitized.

The electrical connections from the eddy current sensor 22 are carried through leads 30 to an eddy current tester 32, such as a Zetec/Automation EM 3300 Eddy Current Tester. The signature appearing on the scope of the tester, as the scanner 6 traverses a tube, will vary depending upon the character of the tube. Thus, followed the usual circuit adjustments, as the eddy current sensor scans a sound portion of the tube, a minor horizontal deflection is obtained representative of sensor wobble, whereas tube abnormalities such as a crack shown at 34 in FIG. 1, will generate on the scope a figure eight pattern from which the location and type of flaw can be determined. In traversing the tube adjacent a support plate, a fat two lobed signature of the support plate is generated as discussed in U.S. Pat. No. 4,194,149 abrupt change in either the horizontal or vertical component of the eddy current signal available at terminals 39, 40 at the nearest support plate can therefore be taken as a bench mark, from which, knowing the speed of the scanner in traversing a tube, the exact location of a tube defect can be determined. To provide proper correlation, as shown, the signals available at terminals 39, 40 are transmitted to the tape recorder 36 and strip chart recorder 38 simultaneously with the readings from the strain gauges.

Figure 7:
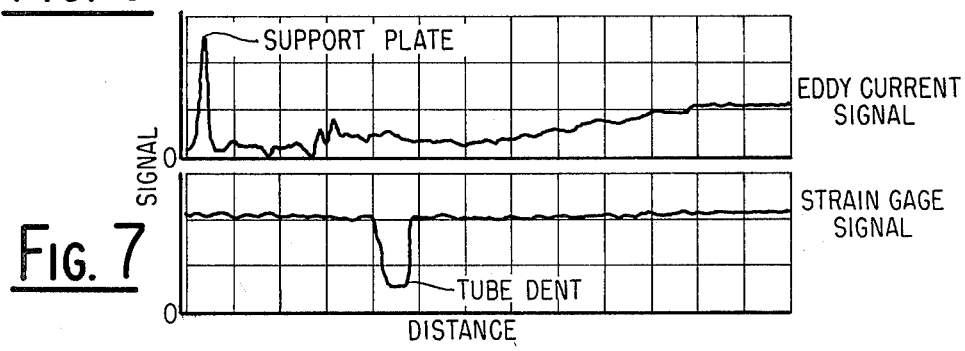
FIG. 7 is a fragmentary view of part of a typical recording of the read-out equipment illustrated in FIG. 6.

In FIG. 7 there is shown a fragment of typical chart traces of one component, either horizontal or vertical, of an eddy current sensor and the signal output of one strain gauge bridge or a single spring finger generated by the composite scanner 6 in traversing a tube. As noted, the eddy current signal abruptly changes at a support plate and provides a bench mark by which, knowing the ratio between scanner and chart speeds, the location of a dent, such as shown at 42 and 43 in FIG. 1, relative to the support plate 4 can be accurately determined. Other tube abnormalities such as variations in diameter out-of-roundness and the like encountered during a traverse can be accurately located. The physical dimensions and contour of the abnormality can be determined by an analysis of the signal outputs as recorded on the tape recorder or the chart recorder 38.

We claim:

1. In an apparatus for inspecting a heat exchanger tube, a scanner adapted to be drawn through the tube having a cylindrical body portion, a first flexure spring having one end anchored to said body portion adjacent its outer circumference and a free end contacting the interior wall of said tube as the scanner is drawn through said tube, a first bi-axial strain gauge connected to said flexure spring having one winding predominantly responsive to the flexing of said flexure spring and the other winding predominantly responsive to the temperature of said strain gauge connected in series across a source of potential, a voltage divider having two windings connected in series across said source of potential and means generating a signal corresponding to the difference in the potentials of the connection between said strain gauge windings and the connection between the voltage divider windings.

2. Apparatus as set forth in claim 1 wherein the two windings of said voltage divider are comprised of the windings of a second bi-axial strain gauge connected to a second flexure spring spaced from said first flexure spring about the circumference of said body portion.

3. Apparatus as set forth in claim 2 wherein the strain gauge windings of the first and second of flexure springs are connected in parallel and in push-pull relationship across said common source of potential.

4. Apparatus as set forth in claim 2 further including a cylindrical shroud secured to said body portion around its outer circumference surrounding said flexure springs and having apertures through which the free end of each of said flexure springs extends.

5. Apparatus as set forth in claim 2 wherein each of said flexure springs is crooked adjacent its free end to form a cusp for contacting the wall of said tube.

6. Apparatus as set forth in claim 1 wherein said first strain gauge is bonded to said first flexure spring.

* * * * *